(12) United States Patent
Schwartz

(10) Patent No.: US 12,053,300 B2
(45) Date of Patent: Aug. 6, 2024

(54) SYSTEM AND METHOD FOR INSTITUTING WELLNESS PRACTICES

(71) Applicant: GrowthWell LLC, Encinitas, CA (US)

(72) Inventor: Drew Schwartz, Encinitas, CA (US)

(73) Assignee: GROWTHWELL LLC, Encinitas, CA (US)

( * ) Notice: Subject to any disclaimer, the term of this patent is extended or adjusted under 35 U.S.C. 154(b) by 0 days.

(21) Appl. No.: 18/080,322

(22) Filed: Dec. 13, 2022

(65) Prior Publication Data

US 2024/0188888 A1    Jun. 13, 2024

(51) Int. Cl.
| | |
|---|---|
| *A61B 5/00* | (2006.01) |
| *A61B 5/0205* | (2006.01) |
| *A61B 5/16* | (2006.01) |
| *G06F 3/04817* | (2022.01) |
| *G06F 3/0482* | (2013.01) |
| *G06F 3/0484* | (2022.01) |

(52) U.S. Cl.
CPC ............ *A61B 5/486* (2013.01); *A61B 5/0205* (2013.01); *A61B 5/165* (2013.01); *A61B 5/7435* (2013.01); *A61B 5/7475* (2013.01); *G06F 3/04817* (2013.01); *G06F 3/0482* (2013.01); *G06F 3/0484* (2013.01)

(58) Field of Classification Search
CPC ........... A61B 5/16; A61B 5/165; A61B 5/486; A61B 5/4884; A61B 5/7264; G09B 7/00; G16H 50/20
USPC ................................................. 434/236, 238
See application file for complete search history.

(56) References Cited

U.S. PATENT DOCUMENTS

| | | | | |
|---|---|---|---|---|
| 2009/0186328 | A1* | 7/2009 | Robinson | ................. G09B 5/14 434/350 |
| 2011/0245633 | A1* | 10/2011 | Goldberg | ............... A61B 5/165 600/323 |
| 2012/0130196 | A1* | 5/2012 | Jain | .......................... A61B 5/45 600/300 |
| 2016/0078778 | A1* | 3/2016 | Holland | ................. A61B 5/746 434/238 |
| 2018/0190147 | A1 | 7/2018 | Chapela et al. | |
| 2020/0350074 | A1* | 11/2020 | Kim | ....................... G16H 10/00 |
| 2022/0066902 | A1* | 3/2022 | Narra | ...................... G16H 20/70 |
| 2022/0133197 | A1 | 5/2022 | Kalra et al. | |
| 2022/0223064 | A1* | 7/2022 | Chauhan | .......... G06Q 10/06395 |

FOREIGN PATENT DOCUMENTS

KR    20220118656 A    8/2022

OTHER PUBLICATIONS

Mood Tracker: Self-Care Habits; Mobile Application available on Google Play; last updated Dec. 9, 2022; retrieved Dec. 12, 2022; https://play.google.com/store/apps/details?id=moodtracker.selfcare.habittracker.mentalhealth.

(Continued)

*Primary Examiner* — Kang Hu
*Assistant Examiner* — Correll T French
(74) *Attorney, Agent, or Firm* — Oliff PLC

(57) ABSTRACT

A system and method for instituting wellness practices. The system will receive information relating to at least one of a psychological or physiological indicator. The system will further provide an output representing at least one recommended action, the at least one recommended action being chosen from a bank of potential recommended actions stored in the at least one memory.

19 Claims, 13 Drawing Sheets

(56) References Cited

OTHER PUBLICATIONS

Heyy, your mental health guide; Heyy PTE. Ltd.; Mobile Application available on Google Play; last updated on Nov. 25, 2022; retrieved on Dec. 12, 2022; https://play.google.com/store/apps/details?id=life.heyy.

* cited by examiner

SYSTEM AND METHOD FOR INSTITUTING WELLNESS PRACTICES

BACKGROUND

Caring for health is an important focus of many individuals and organizations. Systems have been developed to aid users in improving their health by prompting meditation, asking questions, and generally improving awareness of health.

Wellness, or the active pursuit of being in good health, can take various forms. Wellness may include any action that supports an individual's well-being.

In some systems, a person's physical health can be improved by creating reminders to perform specific actions (e.g., diet or exercise) that may improve or at least bring awareness to a person's physical health needs.

Wellness can also be applicable to a person's active pursuit of mental or emotional health. Some current systems include computer-based software to remind a person to take certain actions that may be beneficial for their mental health, including providing an opportunity for therapy. Some systems also provide certain recommendations for self-assessments. However, current systems are deficient insofar as they fail to dynamically link psychological and/or physiological data with wellness activities. Further, current systems lack any process to present different activities based upon learned associations between emotions and activities.

SUMMARY

Embodiments of the instant application relate to a system and method for instituting wellness practices. The system dynamically links personalized user states, personalized wellness practices and aggregated wellness states and practices to help individuals and groups learn and activate powerful wellness outcomes. The instant application further enables each user and group (e.g., organization) to develop their own dynamic wellness algorithm, using real-time data analysis, to promote wellness. Examples of wellness states include, but are not limited to psychological and physiological factors like emotions, heart rate, blood pressure, and so on.

The system described in more detail herein can help a person dynamically link (understand and apply useful tools) between their psychological and/or physiological needs and personalized information and activities that promote wellness. The instant application can take into account, for example, the person's emotions or other psychological or physiological characteristics and incentivize or aid the person to perform wellness practices on a regular basis, and provides the person with activities to perform that may improve the person's mood and/or overall wellness by taking into consideration their emotions and what has helped them (or others) the most based upon past data, including both data relating to the specific person and aggregated data of other persons. The system may also utilize historical data regarding any or all of the emotions as felt by the person or others, as well as the person's or others' response to an activity.

Embodiments of the instant application include a computer-implemented system that utilizes one or more processors to present options of activities in response to a particular psychological and/or physiological input or other data, using stored data and optionally using empirical data relating to the emotion and/or activities. The computer-implemented system may further assess the person's response to the activities and utilize the assessment in creating the empirical data for later use. Further, the computer-implemented system may allow for the person and/or an organization such as a business, organization, school or large scale network or government, to receive raw data and/or processed data in order to learn about the culture and climate of the organization including an individual's psychological and/or physiological data such as what emotions people are feeling, and what wellness practices and activities have been most helpful for particular members of the organization or the organization as a whole.

In some embodiments, a system for instituting wellness practices is described. The system includes at least one processor and at least one memory. The at least one processor receives information relating to at least one of a psychological or physiological indicator (e.g., a psychological indicator, a physiological indicator, or both). The at least one processor is further programmed to provide an output representing at least one recommended action, the at least one recommended action being chosen from a bank of potential recommendation actions stored in the at least one memory.

In some embodiments, the system is programmed to initiate display of a plurality of selectable emotion icons on a graphical user interface. The at least one processor is further programmed to receive a selection of one of the plurality of selectable emotion icons, and to initiate display, on the graphical user interface, of a first plurality of selectable action icons. The first plurality of selectable action icons are chosen from a bank of a second plurality of selectable action icons stored in the memory. The first plurality of selectable action icons are determined based upon the receive selection of the one of the plurality of selectable emotion icons. The first plurality of selectable action icons is smaller in number than the second plurality of selectable action icons.

In some embodiments, a computer-implemented method for aiding in wellness is described. The method includes receiving information relating to at least one of a psychological or physiological indicator (e.g., a psychological indicator, a physiological indicator, or both). The method further includes providing an output representing at least one recommended action, the at least one recommended action being chosen from a bank of potential recommendation actions stored in the at least one memory.

In some embodiments, the method includes displaying a plurality of selectable emotion icons on a graphical user interface. The method further includes receiving a selection of one of the plurality of selectable emotion icons. The method further includes displaying a first plurality of selectable action icons. The first plurality of selectable action icons are chosen from a bank of a second plurality of selectable action icons. The first plurality of selectable action icons are determined based upon the receive selection of the one of the plurality of selectable emotion icons. The first plurality of selectable action icons is smaller in number than the second plurality of selectable action icons.

DETAILED DESCRIPTION OF EMBODIMENTS

Figure 1:
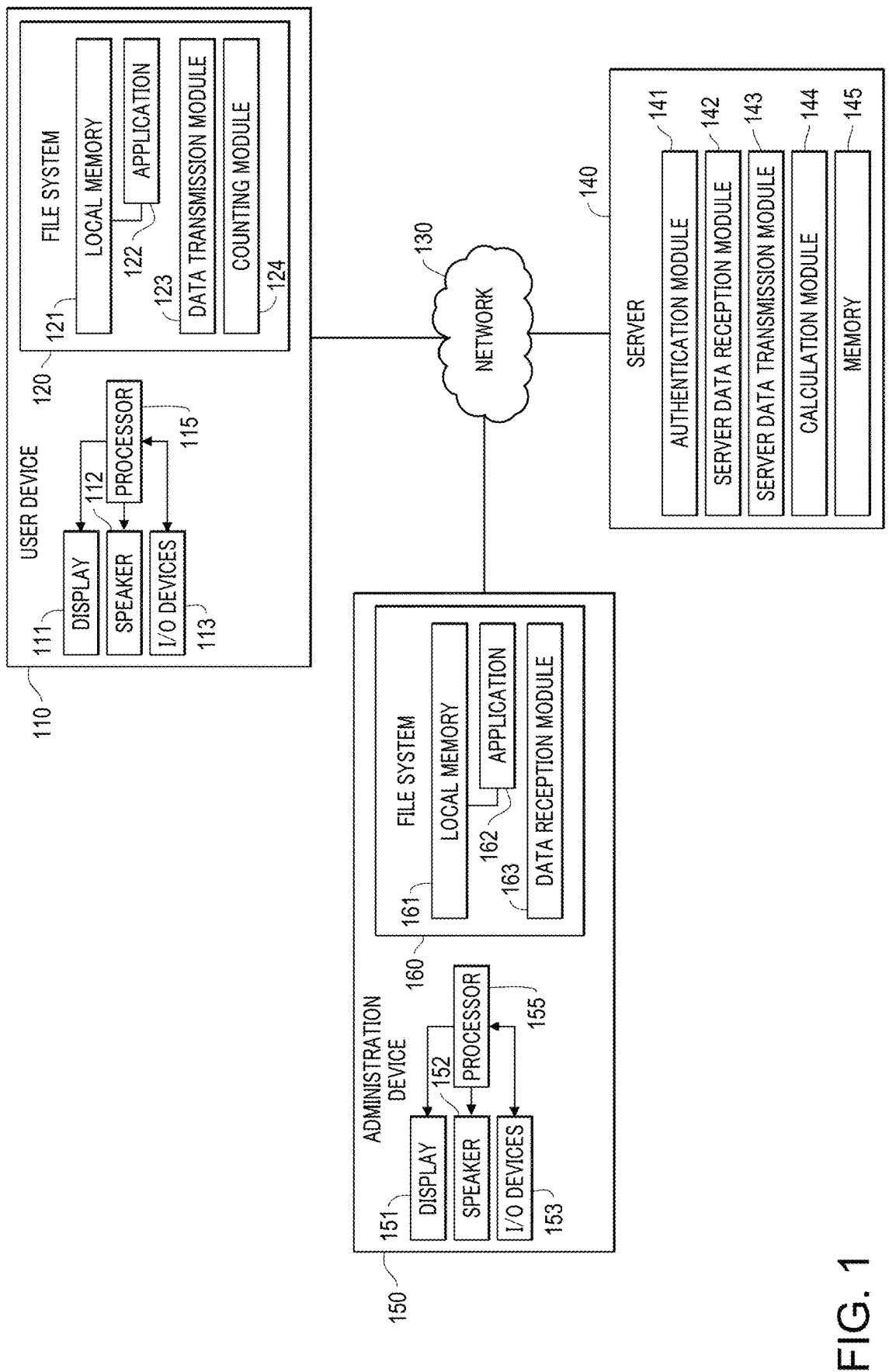
FIG. 1 is a block schematic diagram of a system implemented with a user device within a network according to some embodiments.

In the following description, numerous details are set forth to provide an understanding of the present disclosure. However, it may be understood by those skilled in the art that the methods of the present disclosure may be practiced without these details and that numerous variations or modifications from the described embodiments may be possible.

At the outset, it should be noted that in the development of any such actual embodiment, numerous implementation-specific decisions may be made to achieve the developer's specific goals, such as compliance with system related and business related constraints, which will vary from one implementation to another. Moreover, it will be appreciated that such a development effort might be complex and time consuming but would nevertheless be a routine undertaking for those of ordinary skill in the art having the benefit of this disclosure. In addition, the device and method described herein can also comprise some components other than those cited. In the summary and this detailed description, each numerical value should be read once as modified by the term "about" (unless already expressly so modified), and then read again as not so modified unless otherwise indicated in context. Also, in the summary and this detailed description, it should be understood that a range listed or described as being useful, suitable, or the like, is intended to include support for any conceivable sub-range within the range at least because every point within the range, including the end points, is to be considered as having been stated. For example, "a range of from 1 to 10" is to be read as indicating each possible number along the continuum between about 1 and about 10. Furthermore, the subject matter of this application illustratively disclosed herein suitably may be practiced in the absence of any element(s) that are not specifically disclosed herein.

The terminology used herein is for the purpose of describing particular embodiments only and is not intended to be limiting of embodiments of the disclosure. As used herein, the singular forms "a", "an" and "the" are intended to include the plural forms as well, unless the context clearly indicates otherwise. It will be further understood that the terms "has," "have." "having." "includes." "including." "comprises" and/or "comprising." when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The explicit description of the present disclosure has been presented for purposes of illustration and description, but is not intended to be exhaustive or limited to embodiments of the disclosure in the form explicitly disclosed. Many modifications and variations will be apparent to those of ordinary skill in the art without departing from the scope and spirit of embodiments of the disclosure. The embodiment was chosen and described in order to best explain the principles of embodiments of the disclosure and the practical application, and to enable others of ordinary skill in the art to understand embodiments of the disclosure for various embodiments with various modifications as are suited to the particular use contemplated.

The following definitions are provided in order to aid those skilled in the art in understanding the detailed description.

As used herein, the term "wellness" relates to a state of being in good health, and particularly an active pursuit of good health. The wellness described herein thus relates to actions that may improve awareness of a person's health, and/or may include steps that, if taken, could actively improve the person's health. The health may encompass aspects of mental health, but is not necessarily limited thereto. For example, within the scope of this disclosure are practices relating to wellness that may, either alone or in combination with improving mental health, be used to improve awareness of or otherwise aid in improving physical health.

As used herein, the term "organization" relates to any single entity or group of people that has a responsibility and/or relationship with one or more persons. The one or more persons may be a part of the organization (e.g., workers within a business organization), or may be persons being overseen or watched by a member of the organization (e.g., the persons may be students within a school, where the organization includes the school itself, or a district of multiple schools). An administrator as used herein is a person or entity having a relationship with the organization and is able to be authorized to view the organization's data.

As used herein, the term processor relates to a hardware processor that functions to perform actions based upon instructions that are stored within a computer, network, cloud, server, or other system. The processor may be implemented as hardware within a computer or other user device, or may perform functions using cloud computing.

As used herein, the term psychological refers to anything that affects or arises in the human mind and is related to the mental and/or emotional state of a person. A psychological indicator, for example, may be anything that indicates or represents how a person may be feeling at a particular time, what a person may be thinking, a combination thereof, and so on. The indicator may be a manifestation on a screen (e.g., a user clicking a button representing an emotion), or a programmed capability of software and/or hardware to directly detect a particular emotion and/or other psychological characteristic using specific techniques. These represent affective psychological factors. Other examples of psychological factors within the scope of this disclosure include any cognitive factors, such as thoughts, cognitive distortions, and other elements relating to cognitive behavioral therapy and thought processes.

As used herein, the term physiological refers to anything that affects a function of a human or other living organism. A physiological indicator, for example, may be anything that indicates or represents some characteristic and/or behavior of the human body, such as blood pressure, heart rate, oxygen levels, blood sugar levels, insulin levels, breathing levels and/or other breathing characteristics, sleep data, and so on. The indicator may be a manifestation on a screen (e.g., a user clicking a button representing some physiological characteristic), or a programmed capability of software and/or hardware to directly detect a particular physiological characteristic using specific techniques, such as blood pressure using a blood pressure monitor/sensor, blood oxygen level using a blood oxygen sensor, pulse using a pulse sensor, glucose level using a glucose sensor, time since eating using manual input and/or a capable sensor, and so on.

Referring to FIG. 1, a system for any one or more of tracking, maintaining, practicing, assessing and monitoring wellness is described. The system includes a user device 110. The user device 110 may be any device that has an ability to be operated by a user, and may be a device having a hardware processor therein. For example, the user device 110 may be a laptop computer, a desktop computer, a cell phone (including a smart phone), a tablet, or any other device that can run an application and/or software related to the wellness system described herein.

In some embodiments, the user device 110 includes a display 111. The display 111 may be in the form of a display screen, such as a display screen on a smartphone, tablet or computer. The display 111 may be configured to display one or more graphical user interfaces described in more detail herein. The graphical user interfaces may be controlled by a combination of software programming utilizing a processor following stored instructions, a user action (such as an input), or a combination of both. The display 111 may also include not only the display screen, but also hardware and/or software implemented, in combination with a processor and I/O devices of the user device 110 described later, to provide the graphical user interfaces and to obtain an input from the user.

In some embodiments, the user device includes input/output (I/O) devices 113. These I/O devices 113 may include, for example, a touch screen to allow for a user to provide input to the system, a keyboard for the same, a mouse, a joystick, and so on. The I/O devices may also include, or the user device may separately include, output devices such as a speaker 112 for outputting an audio response based upon user or processor instruction, other displays or subdisplays, and other output device.

The user device 110 also includes a processor 115. The processor 115 may be a hardware processor, such as a central processing unit or CPU, and may be operatively connected to memories such as the local memory 121 within file system 120, or another memory provided somewhere within network 130 or an auxiliary device such as administration device 150 and local memory 161, described later. The processor 115 may be capable of performing steps utilizing instructions stored in the local memory 121 or another memory, utilizing user input, or a combination of the two.

The user device 110 includes a file system 120 with a local memory 121. An application (app) 122 may be stored in the local memory 121 or otherwise accessible from somewhere within the file system 120. In some embodiments, the application 122 is an app that allows the user and/or another user (such as an organization or administrator) to perform the actions relating to wellness described in more detail below.

The file system 120 may have a data transmission module 123. The data transmission module 123 may be a module that can take the data stored in the local memory 121 or otherwise acquired using the processor 115 of the user device 110, and transmit the information elsewhere in the network 130, to which the processor 115 and user device 110 is connected. The transmission from the data transmission module 123 may be directly to the server 140 (e.g., received by server data reception module 142), to the data reception module 163 of the administration device 150, or elsewhere within the network. The data transmission module may be implemented by the processor 115, and may include transmission hardware such as a gateway, interfaces, and so on to ensure transmission of data. In some embodiments, the data may be stored on a cloud server.

The file system 120 also includes a counting module 124. This may be a module of the processor 115, or its own module utilizing a different hardware processor. In some embodiments, the counting module 124 will count each time a wellness practice (described in more detail with respect to later Figures) occurs, and will keep a running tally of the number of times an emotion is acknowledged, an action is taken, or both, for a predetermined period of time. The predetermined period of time may be a month, a week, or an infinite period of time. That is, the counting module 124 may also count event occurrences indeterminately.

Also connected to network 130 is server 140. The server 140 may include its own server memory 145 and may be capable of storing either within the server, on a cooperatively connected cloud server, or remotely, data received from one or more of the user device 110 and administration device 150.

In some embodiments, the server 140 will include an authentication module 141. The authentication module may be utilized to ensure that a user accessing or entering the user device 110 or the administration device 150 is authenticated. That is, at a predetermined time, for example when an app having wellness data is accessed, the server 140 and authentication module 141 may instruct the user device 110 or administration device 150 to require authentication. This may be in the form of a login screen requesting a login ID and a password, a token, supplementary authentication such as an access code, a QR code, and the like. The authentication module 141 may compare the inputted authentication information to stored information within the server memory 145 or otherwise and determine whether or not the user is authenticated to use the user device 110, or the administrator is authenticated to use the administration device 150, as appropriate. In some instances, if the authentication fails, the user or administrator will be prohibited from accessing any of the wellness data for a predetermined time or until authentication is successful.

While the embodiment above described a server 140 having an authentication module 141, the authentication need not necessarily be hosted by the server 140. In some embodiments, the user device 110 will have its own authentication module and stored authentication data, and the user authentication can occur using an analysis by the user device 110 itself. Similarly, in some embodiments, the administration device 150 will have its own authentication module and stored authentication data, and the administrator authentication can occur using an analysis by the administration device 150 itself.

Given the confidentiality of data relating to wellness practices, it may be desirable for only a licensed administrator (e.g., a HR professional in an organization, a school principal or counselor, or district superintendent or the like) to access the information. Thus, in some embodiments, authentication of the administrator is particularly advantageous when considering whether to access the wellness data accessible by the administration device 150.

The administration device 150 may include a display 151. The display 151 may be in the form of a display screen, such as a display screen on a smartphone, tablet or computer. The display 151 may be provided with one or more graphical user interfaces described in more detail herein. The graphical user interfaces may be controlled by a combination of software programming utilizing a processor following stored instructions, a user action (such as an input), or a combination of both. The display 151 may also include not only the display screen, but also hardware and/or software implemented, in combination with a processor and I/O devices of the administrator device 150 described later, to provide the graphical user interfaces and to obtain an input from the user.

In some embodiments, the administrator device includes input/output (I/O) devices 153. These I/O devices 153 may include, for example, a touch screen to allow for the administrator to provide input to the system, a keyboard for the same, a mouse, a joystick, and so on. The I/O devices may also include, or the administrator device may separately include, output devices such as a speaker 152 for outputting an audio response based upon user or processor instruction, other displays or subdisplays, and other output device.

The administrator device also includes a processor 155. The processor 155 may be a hardware processor, such as a central processing unit or CPU, and may be operatively connected to memories such as the local memory 161 within file system 160, or another memory provided somewhere within network 130 or an auxiliary device such as user device 110 and local memory 121, described later. The processor 155 may be capable of performing steps utilizing instructions stored in the memory 161 or another memory, utilizing user input, or a combination of the two.

The administrator device 150 includes a file system 160 with a local memory 161. An application (app) 162 may be stored in the local memory 161 or otherwise accessible from somewhere within the file system 160. In some embodiments, the application 162 is an app that allows the administrator to view, assemble, or otherwise manipulate compiled data relating to wellness described in more detail below. The compiled data may be received by data reception module 163, e.g., received from somewhere within the server by its server data transmission module 143, or the user device 110 and its data transmission module 123.

The server 140 further includes a calculation module 144. The calculation module 144 may be a functional unit of a separate hardware processor within the server 140, or may be otherwise controlled using processor 115 or 155. Further, though shown within the server 140, the calculation module 144 may also be locally hosted within the user device 110 or administration device 150, as appropriate.

The calculation module 144 is able to run complex calculations unique to the data being presented. For example, the calculation module 144 will be able to analyze emotions selected by a user, actions selected by a user, and can perform real-time algorithms to improve wellness practices offered to the user or to another user. The calculations can also improve the graphical user interface shown on the display 111 of the user device 110 and/or the display 151 of the administration device 150, by presenting choosing icons most likely to represent a positive result, and presenting icons in a colored, sequenced manner that can aid in user selection. Further, the data may be presented on the display 151 in such a manner that can allow for real-time assessments to be made regarding wellness practices for a larger subset of users, so that an organization can advantageously make appropriate arrangements. Details of the analysis that can be run by the calculation module 144 will be described with reference to FIGS. 2-14, below.

In the implementations described herein, one or more of the processor 115, a processor of the server, and the processor 155 will cause the display 111 (or display 151, as appropriate) to display the relevant information.

Figure 2:
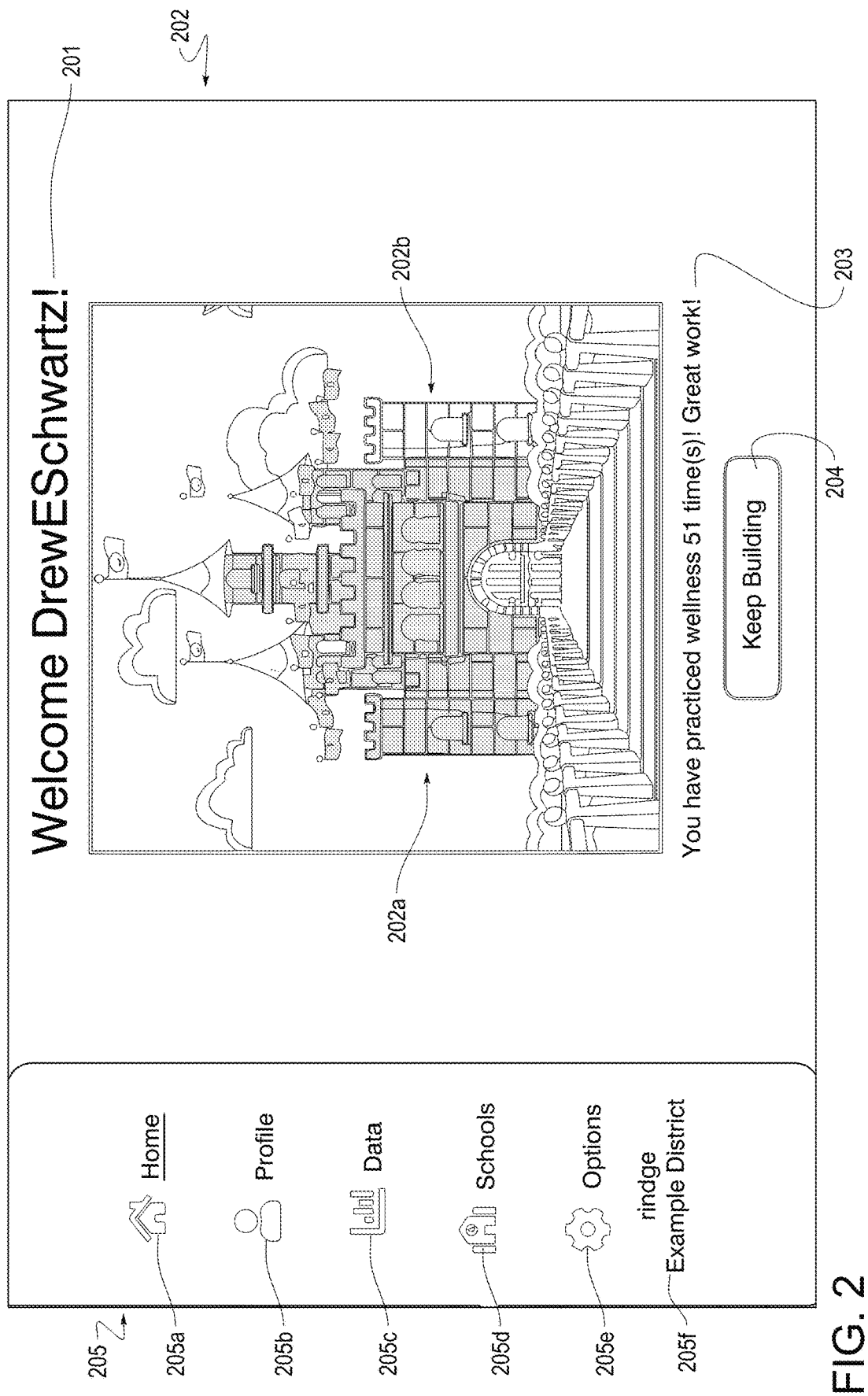
FIG. 2 is an exemplary display of a home screen according to one or more embodiments.

Referring to FIG. 2, a home screen for the wellness application is provided. While this may be a home screen of the user device 110 (e.g., shown on display 111, subsequent to an instruction to do so by processor 115), and is discussed with reference to the same, a similar or identical home screen may be provided on a display 151 of the administrator device 150.

The home screen may include a welcome identifier, where a name or user ID 201 is shown. The name or user ID 201 may change depending on which registered user is accessing the wellness application.

Shown also on the display 111 is an image 202. The image may be the image of a castle, as shown, or some other image. In some embodiments, the image will include a colored portion 202a and an incomplete portion 202b. Further, a counter 203 may be provided. The counter 203 may provide a numerical indication of how many times the user has practiced wellness (e.g., by completing the steps requested by the app) in a predetermined amount of time, such as within a week or a month, or in an infinite time period. In the example shown herein, the user has performed wellness 51 times in the predetermined period, as indicated by counter 203.

In some examples, the amount of the image 202 shown as colored portion 202a relative to incomplete portion 202b corresponds to the amount of wellness practice completion indicated by the counter 203 as compared to a predetermined target. For example, if a target of 60 wellness practices is set and 51 wellness practices have been completed as indicated by counter 203, then roughly 51/60 of the image 202 will be colored and shown as colored portion 202a, while the remaining 9/60 of the image 202 will be uncolored and showed as incomplete portion 202b. As described later, as wellness practices are completed by the user, more of the image 202 will be represented as colored portion 202a and less of the image 202 will be represented by incomplete portion 202b, until the target is reached, at which time the image will reset and become entirely represented by an incomplete portion 202b.

In some instances, the counter 203 will not directly correspond to the amount of the image 202 represented by the colored portion 202a, as the target may change and the counter 203 may represent a different number than an amount of wellness compared to such a target.

Also shown in FIG. 2 is a menu 205, which includes a home button 205a. The home button 205a will take the user to the home screen, which is the screen of FIG. 2. However, this home button 205a will be shown in the menu when then user is viewing other screens, thus allowing an immediate redirection to the home screen. A profile button 205b will allow the user to access and optionally edit his/her profile. A data button 205c will allow the user to access his/her data, as described later. A schools button 205d will allow for data relating to schools or other organizations to be shown. This may be viewable to a particular user, or may be only viewable to a registered administrator, including one that uses the administrator device 150.

The menu 205 also includes an options button 205e, which allows for the user to view and/or change predetermined settings relating to the display or components of the application in general.

The menu 205 also includes an indicator 205f. The indicator 205f shows the broader organization (for example, school, school district or business) that the user is associated with.

The home screen also includes a continue button 204, represented as a "keep building" button. Once button 204 is pressed by the user, or after a predetermined amount of time, the application will move to the display 111 represented by FIG. 3.

Figure 3:
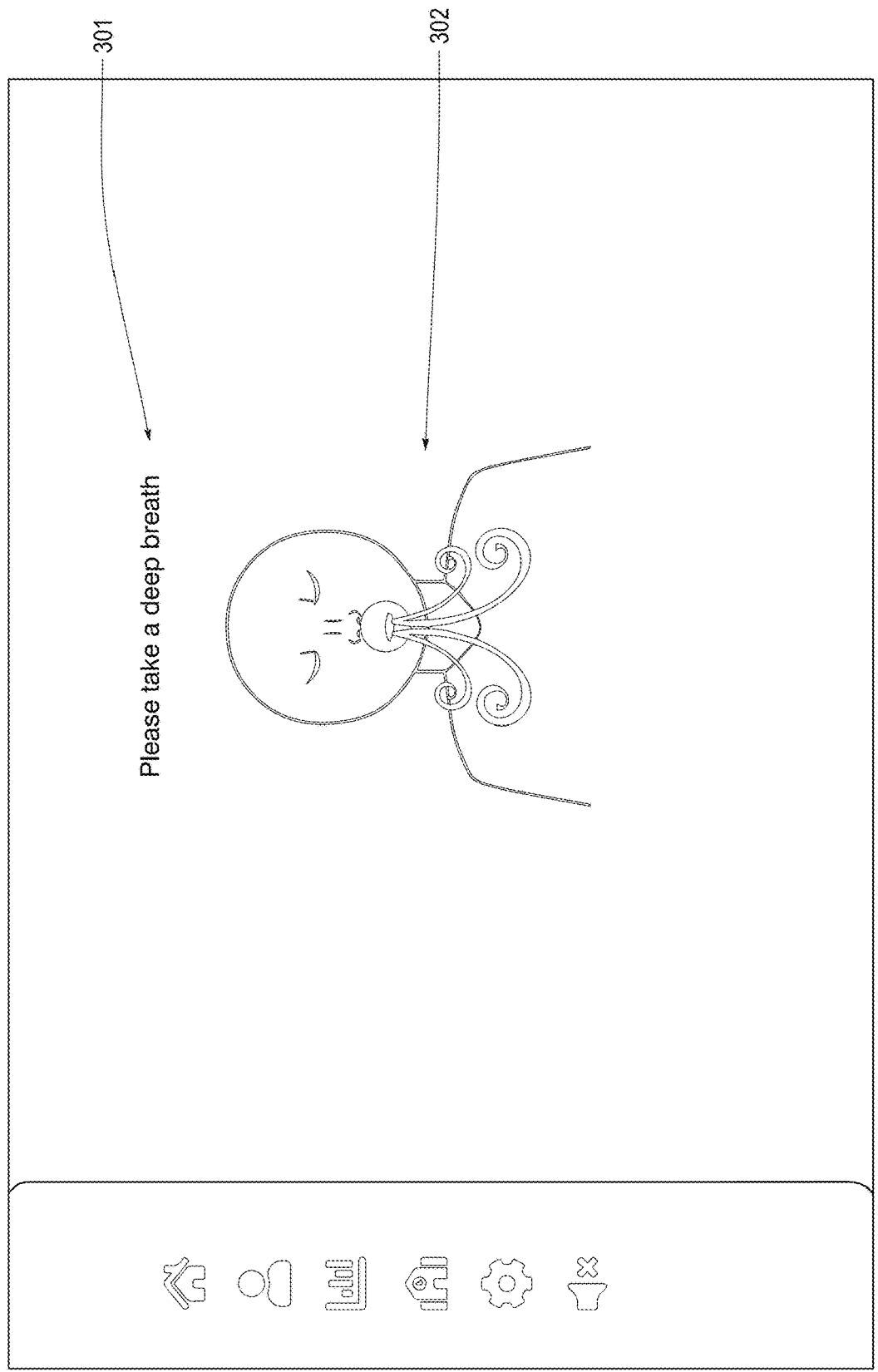
FIG. 3 is an exemplary display of an initial wellness practice according to one or more embodiments.

Referring to FIG. 3, the user is instructed to take an action, such as to take a deep breath, represented by instruction 301. Instruction 301 may always request the user to take a deep breath, or may provide another predetermined instruction relating to a wellness practice determined to be applicable for a particular user or for people generally. The display 111 may also include an associated image 302, the associated image 302 being associated with the instruction 301. The associated image 302 may serve as a reminder and/or motivation for the user to perform the instruction 301. Further, while shown, the representation of FIG. 3 is an optional feature of the application and may be omitted.

Figure 4:
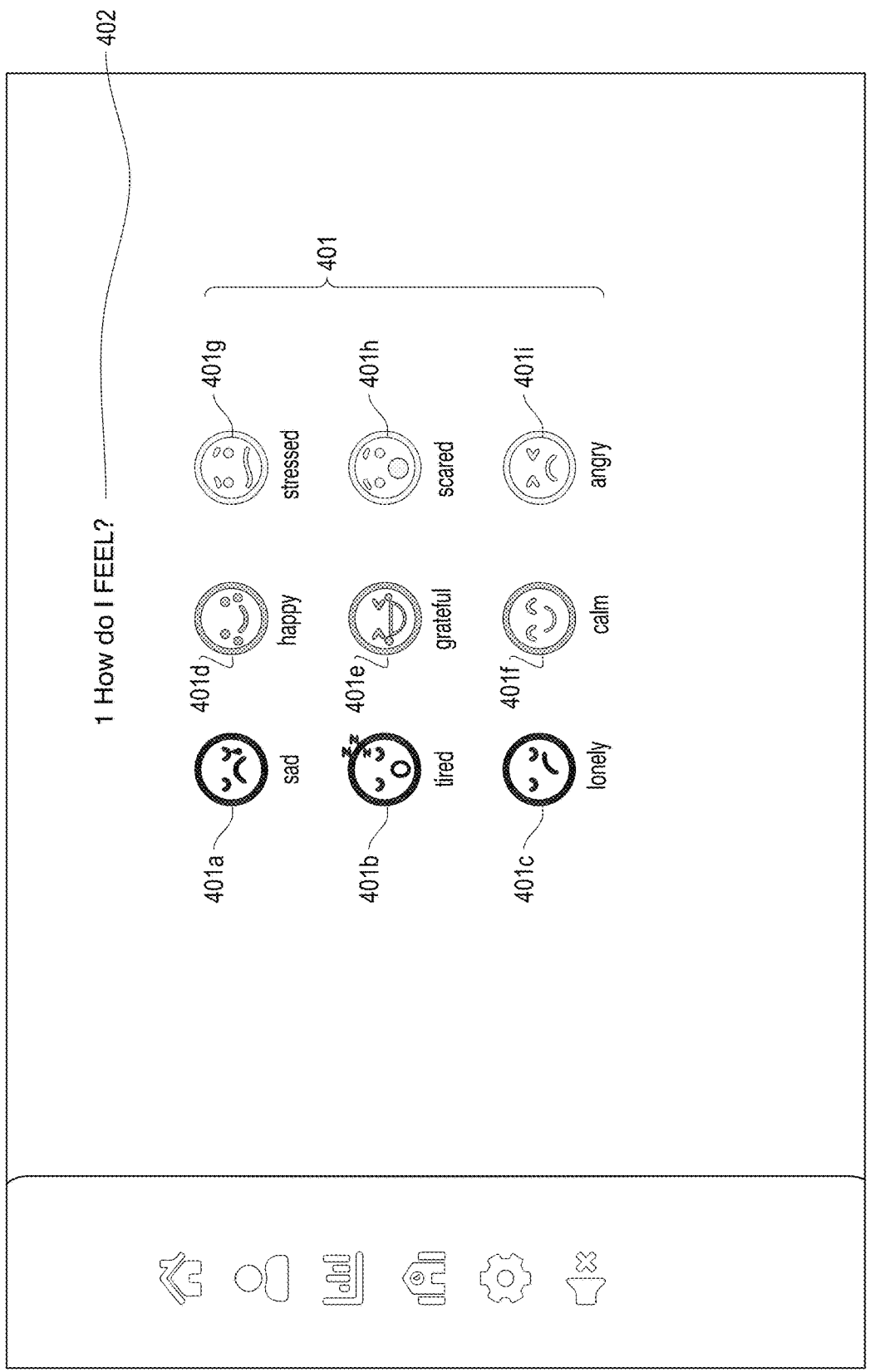
FIG. 4 is an exemplary display of selectable emotion icons having associated emotions according to one or more embodiments.

After a predetermined period of time, or once the user indicates to continue either by clicking or tapping the screen, a continue button (not shown), or speaking a command to continue, the application will continue to the display represented by FIG. 4.

Shown on the display 111 of FIG. 4 is a question 402. The question, in this case, is "How do I FEEL?" However, the question 402 is not so limited and may change to another predetermined question requesting input from the user.

Shown on the display 111 are a series of selectable emotion icons 401a-i. The selectable emotion icons 401a-i are selectable by the user and represented as a graphical user interface provided on the display 111. In some instances, the icons are grouped into emotions that share similar characteristics. For example, the first column of selectable emotion icons 401a-c may be considered a first group of selectable emotion icons and may be represented by a first color. Each icon, including sad 401a, tired 401b, and lonely 401c, may share similar characteristics, in this case being an emotion with a somewhat negative association. Each selectable emotion icon 401a-c may be represented as a clickable or touchable image, along with a text representation (that may or may not also be clickable or touchable) that corresponds to the image.

The second column of selectable emotion icons 401d-f may be considered a second group of selectable emotion icons and may be represented by a second color different from the first color. Each icon, including happy 401d, grateful 401c and calm 401f, may share similar characteristics, in this case being an emotion with a somewhat positive association. Each selectable emotion icon 401d-f may be represented as a clickable or touchable image, along with a text representation (that may or may not also be clickable or touchable) that corresponds to the image.

The third column of selectable emotion icons 401e-g may be considered a third group of selectable emotion icons and may be represented by a third color different from the first color and from the second color. Each icon, including stressed 401g, scared 401h and angry 401i, may share similar characteristics, in this case being an emotion with a somewhat heightened sense. Each selectable emotion icon 401e-g may be represented as a clickable or touchable image, along with a text representation (that may or may not also be clickable or touchable) that corresponds to the image.

While each column of selectable emotion icons 401a-i are shown in different colors from the others, the icons may also be in the same colors, or may have their colors divided differently.

Figure 5:
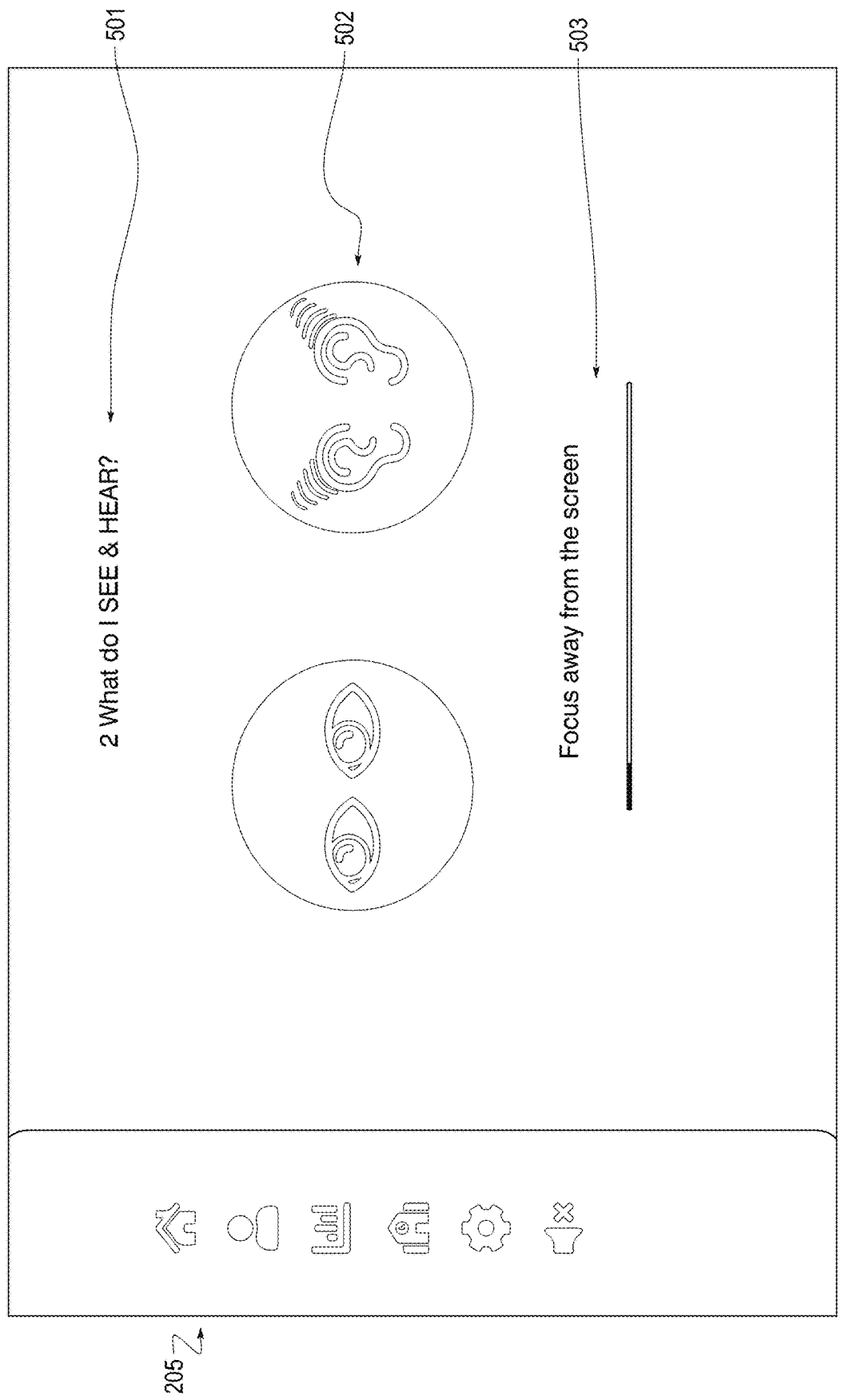
FIG. 5 is an exemplary display of a prompt according to one or more embodiments.

Once a user selects one of the selectable emotion icons 401a-i, or after a predetermined time after the selection is made, or upon the user instructing to continue using voice or touch commands, the application will continue to the display represented by FIG. 5.

FIG. 5 initiates a display 111 with further instructions to the user. For example, FIG. 5 includes a further question 501, which, in this case, is "What do I SEE & HEAR?" This is merely representative of one further question 501, and other further questions 501 may be presented as necessary. The further question 501 is a question that generally prompts a user to become aware of his/her surroundings and to practice mindfulness and to mindfully ground his/her senses.

The display 111 also optionally shows a plurality of images 502 having an association with the further question 501. At the bottom of the screen, or at any other appropriate location, is a further instruction 503, in this case prompting the user to focus away from the screen. The application may wait a predetermined period of time before moving to the next screen, or may do so once the user indicates to continue either by clicking or tapping the screen, a continue button (not shown), or speaking a command to continue. Further, while shown, the representation of FIG. 5 is an optional feature of the application and may be omitted.

Figure 6:
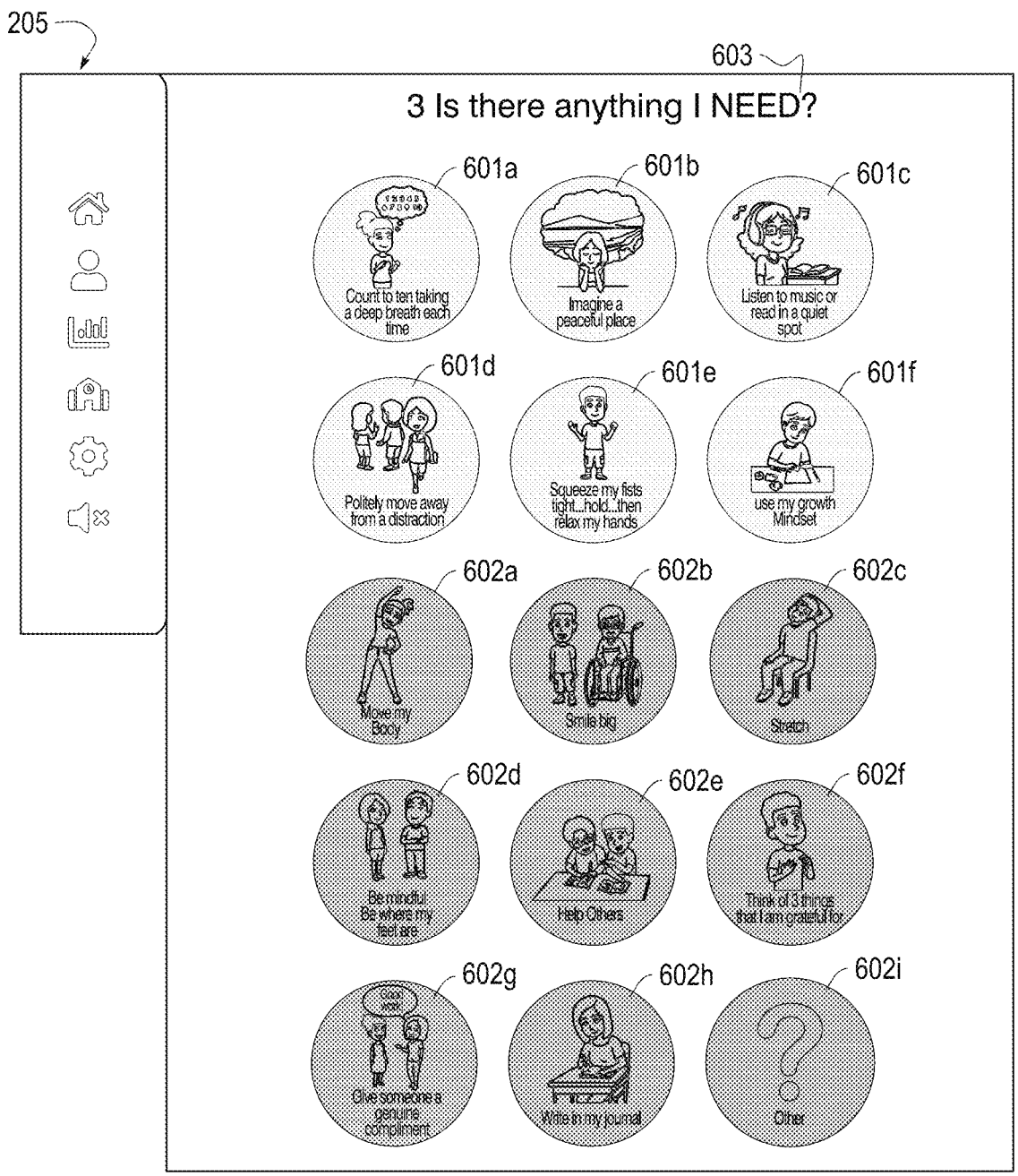
FIG. 6 is an exemplary display of selectable action icons according to one or more embodiments.

The processor 115 or another hardware processor then instructs the display 111 to present a further graphical user interface to the user, as represented in FIG. 6. The display may include a still further question 603, such as "Is there anything I NEED?" This still further question 603 prompts the user to select a particular action, as represented in the plurality of displayed selectable action icons 601a-f and 602a-i (hereinafter represented together as 601, 602).

Based upon previously input data and/or data otherwise assessed by the calculation module 144, the displayed selectable action icons 601, 602 are dynamically presented. In this case, the selectable action icons include actions such as count to ten taking a deep breath each time 601a, imagine a peaceful place 601b, listen to music or read in a quiet spot 601c, politely move away from a distraction 601d, squeeze my fists tight . . . hold . . . then relax my hands 601e, use my growth mindset 601f, move my body 602a, smile big 602b, stretch 602c, be mindful. Be where my feet are 602d, help others 602e, thing of 3 things that I am grateful for 602f, give someone a genuine compliment 602g, write in my journal 602h, and other 602i. In some embodiments, these displayed selectable action icons 601*a-f* and 602*a-i* may be a first plurality of selectable action icons which are icons (with their associated actions) that are a subset of a larger data bank of selectable action icons, such as a second plurality of selectable action icons. How the processor 115 (or other processor) chooses the displayed selectable action icons 601, 602 and instructs the display 111 them is a subject of the methods of this application.

In some embodiments, the displayed selectable action icons have a relationship with the selected emotion icon. For example, if the user were to select "sad" in FIG. 4, the processor 115 (or server processor) would search the data bank of selectable action icons, which is stored in a memory (either the local memory 121 or a memory 145 within the server), and determine which of the selectable action icons has a known association to the emotion "sad." If necessary, the processor 115 would communicate with the server 140 to transmit and/or receive the necessary data.

In some instances, each of the selectable action icons in the data bank will have a rank for each of the potentially chosen emotions, and, based upon the rank and chosen emotion, the processor will instruct display of the selectable action icons that are the most highly ranked candidates for that emotion. As an example, the graphical user interface may include about 10, about 12, about 15 or about 20 selectable action icons 601, 602 on the display 111. As an example, 15 selectable action icons 601, 602 are shown.

If the emotion "stressed" is chosen by the user on the graphical user interface shown in the display 111 in FIG. 4, the 15 most highly ranked selectable action icons will be displayed. The icons may be shown in predetermined colors. Those with a highest association to the emotion may be shown in the same color as the emotion. For example, if the user were to have chosen "stressed" in FIG. 4, the top six selectable action icons 601, 602 (e.g., 601*a-f*) may be shown in the third color, which corresponds to the color of "stressed." Other selectable action icons (e.g., 602*a-i*) may be shown in another color, for example the second color, if they are more highly ranked for emotions that were shown in the second column of FIG. 4. In some instances, all of the selectable action icons 601, 602 are shown in the same color, which may be the color corresponding to the selected selectable emotion icon 401, or another color.

Further, as described in more detail later, the system, particularly using the server 140 and the server data reception module 142 and calculation module 144, may receive information from the user about how helpful a wellness practice (action) corresponding to the selected action icon was. This may be inputted or stored either locally at memory 121 or on the server at server memory 145 as a particular numerical value (e.g., 1 if helpful, 0 if not, or some other numerical value). The value may also simply be a "yes/no" understanding where the system can associate whether or not the action was considered to be helpful in a non-numerical fashion, such as using a flag or the like, so long as a "yes" understanding can be easily discriminated from a "no" understanding by the system. If the wellness practice was considered to be helpful, it may be shown as a selectable action icon next time the same emotion is chosen by the user. It also may be more likely to be shown when other similar emotions are chosen by the user. That is, its rank may dynamically change based upon whether or not the emotion was deemed helpful. The rank may dynamically change based upon other data relating to others within the broader organization stored within the server 140 or otherwise, or based upon any other learned or input data.

In some instances, the calculation unit will weight user input with a first weighting, organizational input with a second weighting, and other input data with a third weighting, and, based upon these weightings, will determine new rankings for each of the selectable action icons. In some embodiments, the first weighting is higher than the second weighting, which is in turn higher than the third weighting. In others, the second weighting is higher than the first weighting, which is in turn higher than the third weighting. In some embodiments, the third weighting is the highest weighting, for example, when something about a particular practice is learned (e.g., if empirical data shows that a wellness practice has a negative effect and should be removed).

Thus, for future uses of the application by the user or even by a different user, the system may or may not instruct display of the same selectable action icons for a same chosen emotion, and the selectable action icons to be shown, such as a third plurality of selectable action icons, will depend on the determinations made by the calculation module and ultimate ranks of the selectable action icons within the data bank based upon the learned and input information. These ranks take into consideration the previous history and iterations of the application, such as which ones of the selectable action icons 601, 602 were selected and/or considered to be help.

Figure 7:
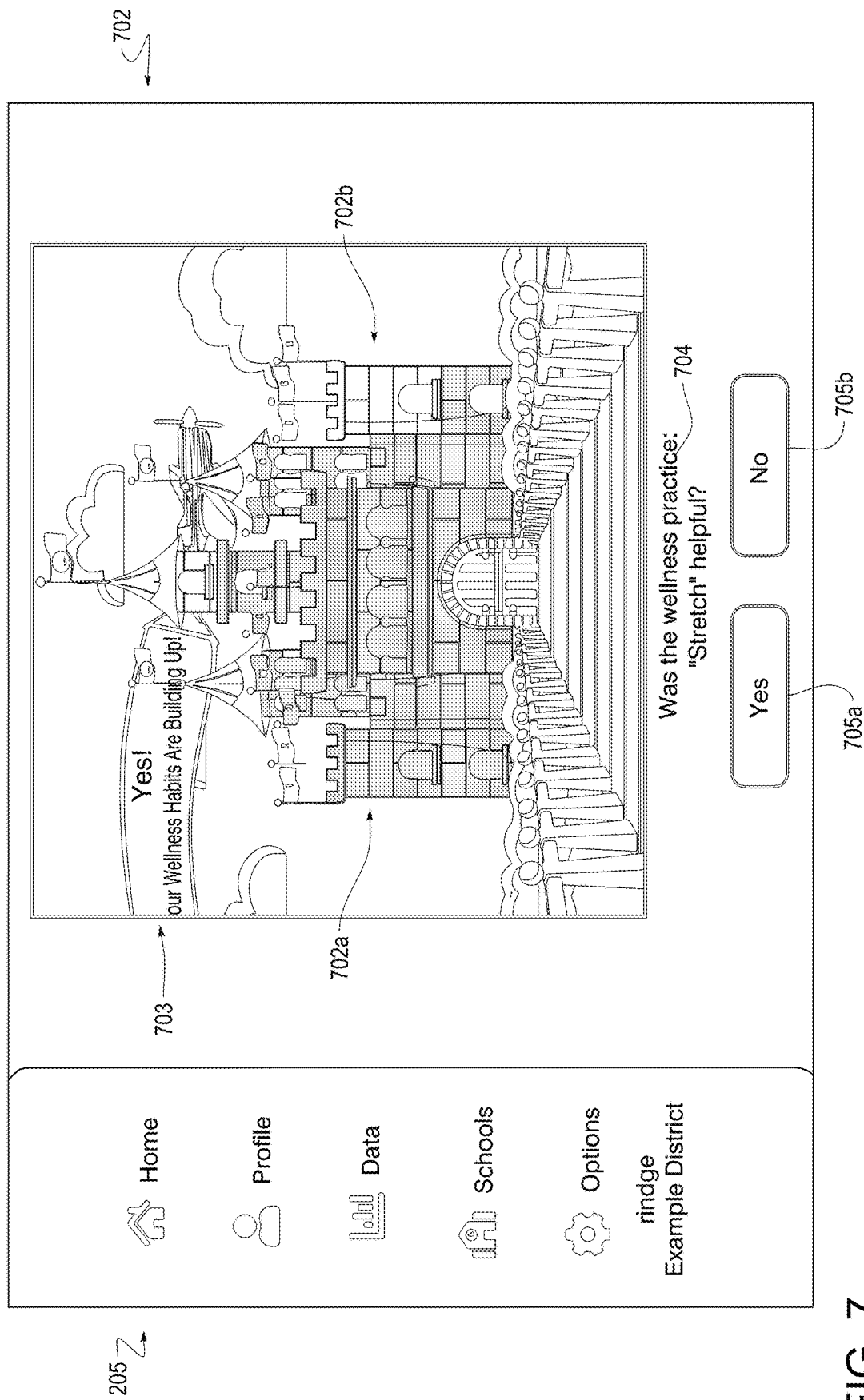
FIG. 7 is an exemplary display subsequent to selection of an action according to one or more embodiments.

As shown in FIG. 7, once selecting a selectable action icon 601, 602, the user may be given some time to practice the wellness practice. A screen with the same image or similar image to that on the home screen may be shown, e.g., with image 702. A motivational indicator 703 may also be provided to inform a user of the positive improvements that can occur in view of the actions taken. Further, based upon the performed action, another portion of the image will be represented as a colored image 702*a*, and less of the image will be shown as an incomplete image 702*b*.

As described above, a graphical user interface will be shown on the display 111, requesting user input as to a helpfulness of the action associated with the selected selectable action icon 601, 602. This may be provided in the form of a question 704 (e.g., "Was the wellness practice: "Stretch" helpful?" to which the user will respond by indicating positively by yes button 705*a*, or negatively by no button 705*b*. The data will then be transmitted by the server data transmission module 123 to the server data reception module 142 of the server 140, and may be converted into a value, so the server can make the appropriate calculations for future ranking of selectable action icons.

While FIGS. 4-7 were described as an implementation where one selectable emotion icon 401 and one selectable action icon 601, 602 were selected by a user, implementations within the scope of this disclosure include where multiple selectable emotion icons 401 are selected, and/or ultimately selectable action icons 601, 602 are selected, with multiple actions subsequently performed. In this case, the system will ensure that both or all emotions and/or actions that are selected are assessed, and will analyze the data in a similar manner as described with respect to FIGS. 4-7.

Further, it is understood that after the processes of FIGS. 2-7 occur, a user can subsequently repeat the same steps of FIGS. 2-7, with the data similarly being processed in the same ways. Further, in the subsequent displays of the selectable action icons 601, 602 of FIG. 6, the calculations described above will initiate a potential modification of selectable action icons 601, 602 as compared to previous times, given the potential change in rankings described above.

Figure 8:
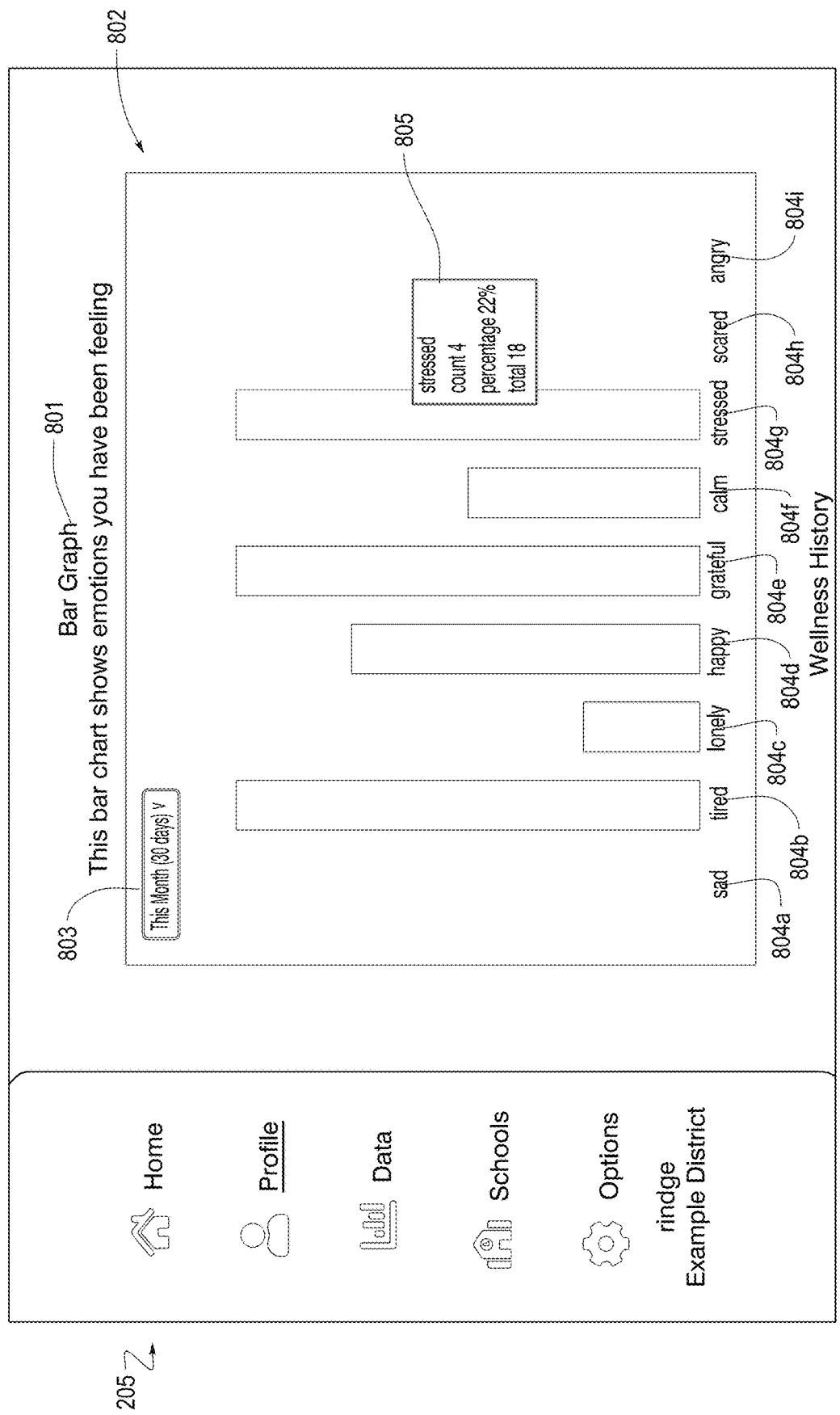
FIG. 8 is an exemplary display of information relating to individual wellness according to one or more embodiments.

FIG. 8 is a representation of data based upon a user's response. This may be found when the user clicks the data button 205c (or tab) on the menu 205. The data in this case is represented by a bar graph having a title 801, with the data represented in graphical form. The bars 802 correspond to a number of times a particular emotion 804a-i was felt (e.g., the user selects a particular one of the selectable emotion icons 401) in a predetermined period of time. The predetermined period of time may be, for example, 30 days as shown in FIG. 8 and as identified by timer 803. Further, the timer 803 may be changeable and the user may be able to show a different time period based upon changing the timer 803 to, for example, one week, six months, one year, or forever or the like. Based upon a timer 803 selection, the processor 115 will accordingly (either alone or in combination with the processor of the server) consult the local memory 121 and/or server memory 145 and display the appropriate data. The display 111 may also include a text box 805 that includes specific data about a particular bar 802, either pursuant to hovering over the bar with a mouse or finger or by clicking or touching the bar. The data in the text box 805 may include the emotion (for example, stressed 804g), a numerical count corresponding to the number of instances of the emotion, a percentage of this emotion compared to other emotions, and a total number of emotions within the timer 803 period.

Figure 9:
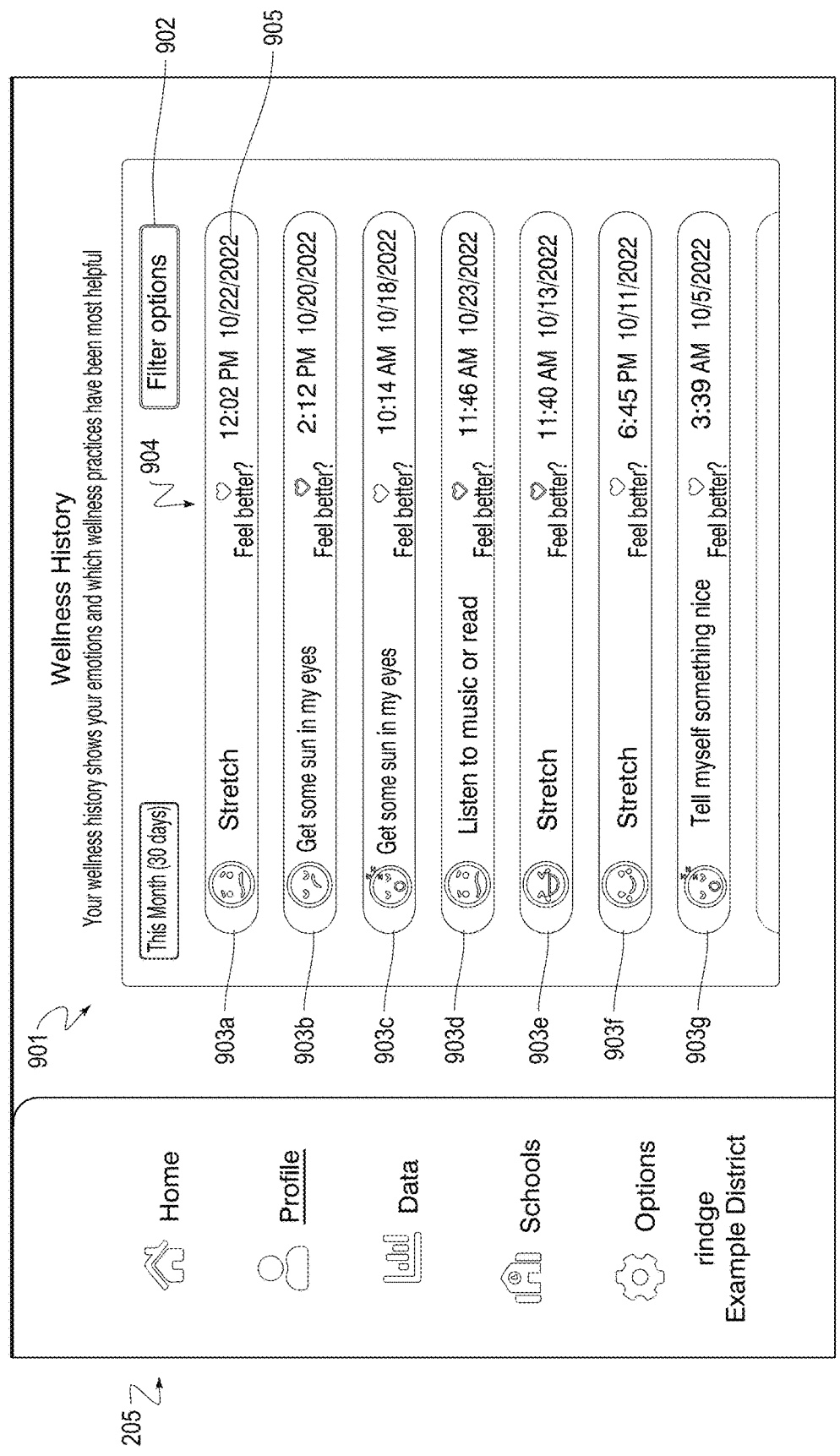
FIG. 9 is another exemplary display of information relating to individual wellness according to one or more embodiments.

FIG. 9 is a wellness history 901 that shows an indication of the selectable action icons that were chosen by the user in a predetermined period of time. This may also include a timer and/or filter 902, which can allow for the display to be manipulated to show more or less of the data, or the data differently.

The data items include items 903a-g, each of which corresponds to a particular selected selectable action icon from FIG. 6. The data items include a representation 904 as to whether the action was helpful (e.g., yes if the heart is filled in, no if not). The representation corresponds to the answer provided by the user to question 704 in FIG. 7.

The data items may also include a timestamp 905 including a time and/or date of when the action was practiced.

Figure 10:
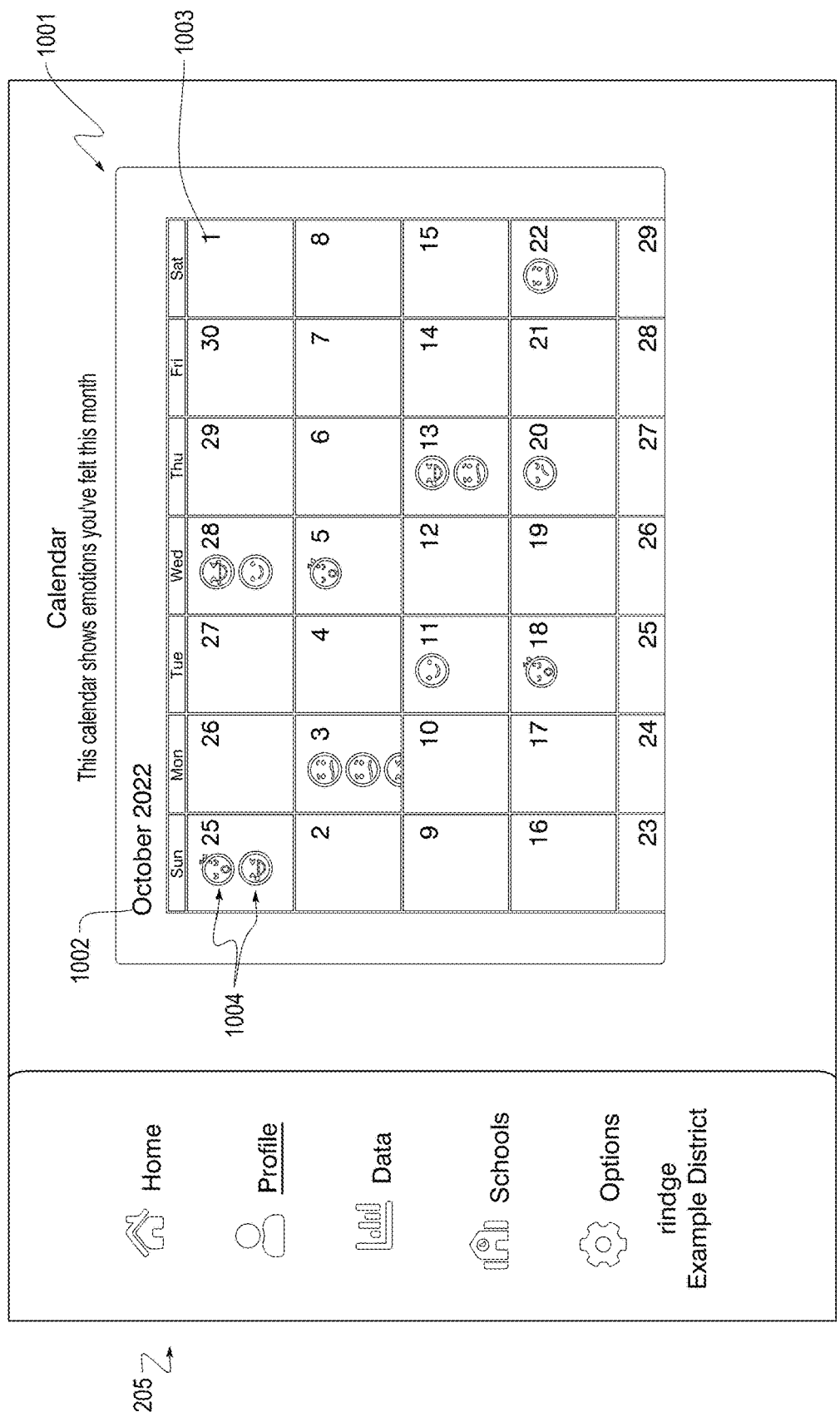
FIG. 10 is an exemplary calendar display of information relating to individual wellness according to one or more embodiments.

FIG. 10 shows a calendar 1001 representation of emotions that were felt in a particular month 1002. The calendar shows particular dates 1003, with emoticons 1004 that correspond to which emotions (e.g., those selected in FIG. 4) were felt when using the application on a particular day. This is another visual aid to help a user understand his/her emotions at a particular time, or over a particular period of time.

Figure 11A:
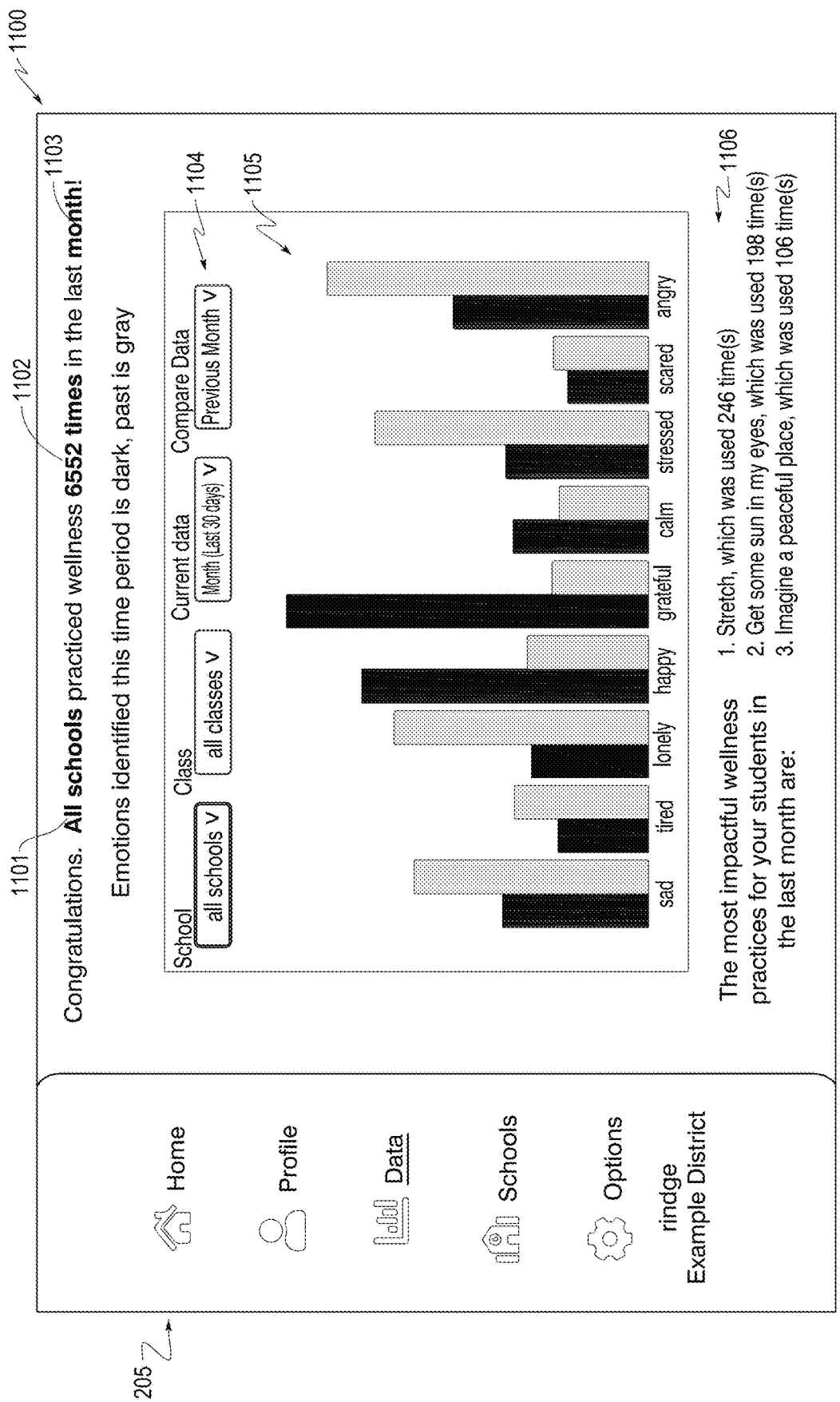
FIG. 11A is an exemplary display of information relating to wellness within an organization according to one or more embodiments.
Figure 11B:
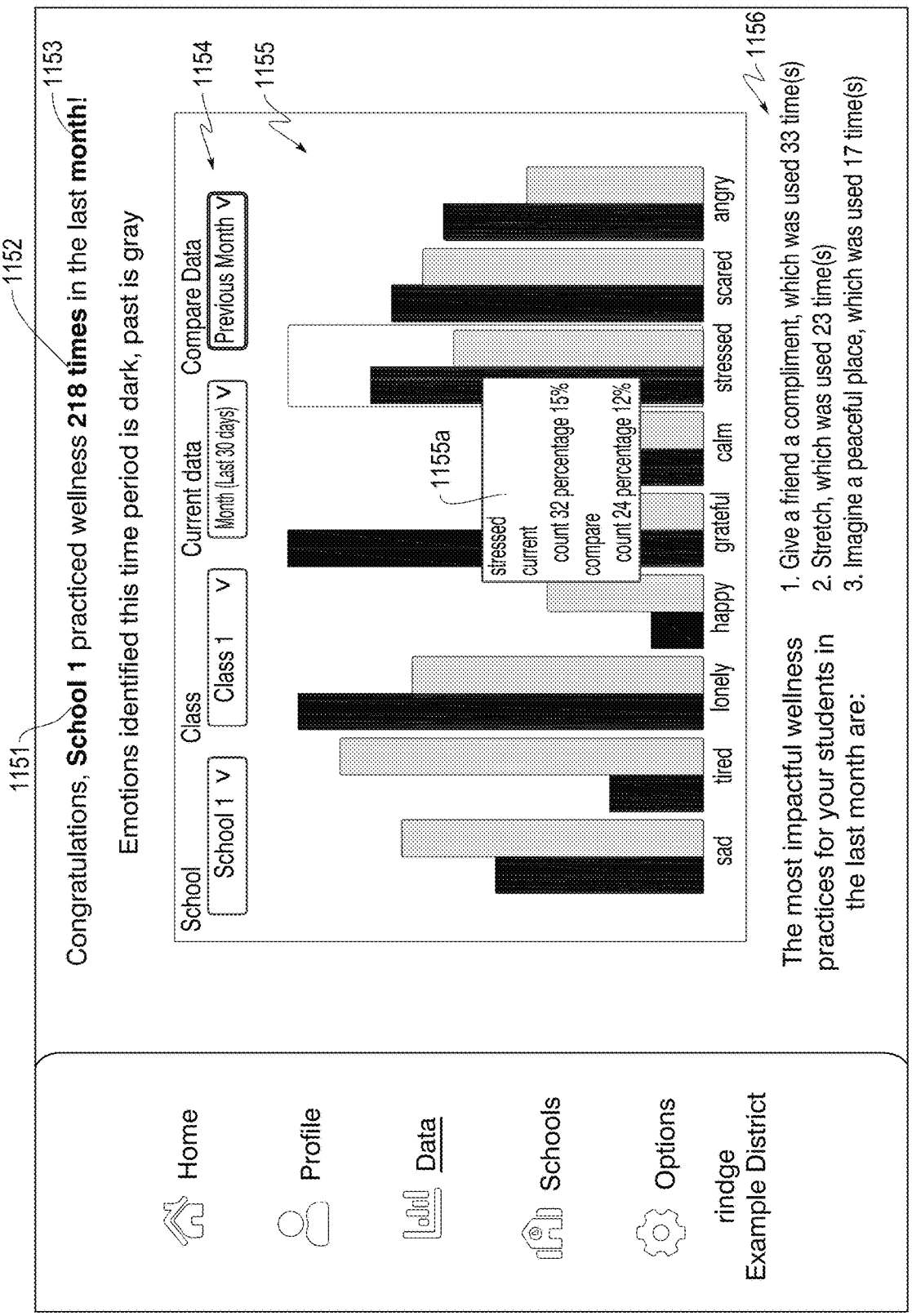
FIG. 11B is another exemplary display of information relating to wellness within an organization according to one or more embodiments.

FIGS. 11A and 11B show organizational data. This may be implemented by processor 155 of the administrator device 150, which may receive data from the server 140, and may be instructed to be shown on display 151. However, a user, if authorized, may also be able to view such data on the user device 110 and display 111.

Referring to FIG. 11A, data 1100 is shown. The data may include an indication 1101 of which members of the organization are being represented by the data, and how many times 1102 the members practiced wellness (e.g., performed one or more processes in the application, for example performing one of the actions in FIG. 6) within a predetermined time period 1103. There may also include filtering options to allow the members to be shown differently (thus changing indication 1101), including for example the school or the class to be changed, and the time period to be changed (thus changing predetermined time period 1103). Further, there may include a compare data filtering option 1104 that allows the bar chart 1105 to show not only the data represented by the other filtering options, but also a comparison data (for example, the previous month). The comparison data may be shown in a different color or in lighter grayscale, as shown in FIG. 11A.

Further, there may include a summary 1106 of the most impactful wellness practices over a particular time period. This may indicate the top, or top 3, or top 5, actions performed based upon the selectable action icons of FIG. 6, across the organization. This may take into consideration how many times the action was performed, or may take into consideration how many times the performed action was determined to be helpful (e.g., "yes" on FIG. 7), or both.

FIG. 11B shows a similar data set where a specific school is shown. The data may include an indication 1151 of which school is being represented by the data, and how many times 1152 the members practiced wellness (e.g., performed one or more processes in the application, for example performing one of the actions in FIG. 6) within a predetermined time period 1153. There may also include filtering options 1154 to allow the members to be shown differently (thus changing indication 1151), including for example the school or the class to be changed, and the time period to be changed (thus changing predetermined time period 1153). Further, there may include a compare data filtering option 1154 that allows the bar chart 1155 to show not only the data represented by the other filtering options, but also a comparison data (for example, the previous month). A text box 1155a may also show particular indications of the hovered-over or selected emotion, a count compared to other emotions, and a comparison to the data being compared in the comparison data. The comparison data may be shown in a different color or in lighter grayscale, as shown in FIG. 11B.

Further, there may include a summary 1156 of the most impactful wellness practices over a particular time period. This may indicate the top, or top 3, or top 5, actions performed based upon the selectable action icons of FIG. 6, across the organization. This may take into consideration how many times the action was performed, or may take into consideration how many times the performed action was determined to be helpful (e.g., "yes" on FIG. 7), or both.

Further and relatedly, once the systems of the instant embodiments acquire the data (e.g., how many emotions or other psychological/physiological indicators were found over a predetermined time, which selectable action icons were chosen, or, in more general embodiments, how many actions were recommended, and also optionally the value the user ascribed to any or all particular actions), the systems may generally, using the above-described processors, aggregate the data and present the user and/or organization and/or subgroup within the organization (for example, a class or small number of classes within a school), with customized strategies based upon an assessment of the aggregate data. Thus, beyond displaying the data, the systems may automatically provide the user or organization with suggested general wellness practices, time-sensitive actions to take, other remedial actions, to more broadly introduce the particular action items considered to be most useful in view of the data and the like.

It will be appreciated that the information provided by the systems described herein may improve the ability of the application itself to provide a more desirable result, such as a more likely to be helpful wellness practice being shown as a selectable action icon 601, 602 in the future, based upon the assessment of data already provided. Further, the data may be useful for organizations to allow them to institute wellness practices or take remedial actions to address emotions that may be occurring across an organization, or to more broadly introduce action items considered to be useful in view of the data.

While fully implemented within the systems described above, some methods of aiding in wellness are described further herein.

Figure 12:
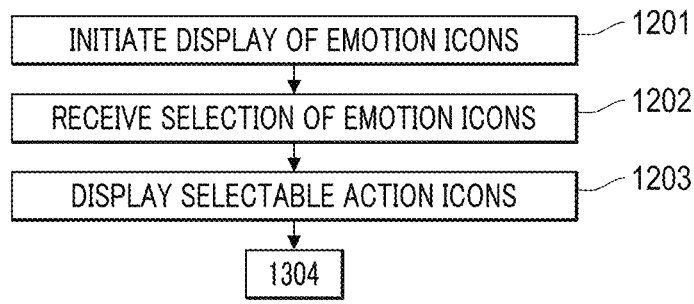
FIG. 12 is a flowchart of an example of a method for aiding in wellness according to some embodiments.

Referring to FIG. 12, the method may include a step 1201 where a processor such as processor 115 or another process initiates display of selectable emotion icons 401. These may be shown as part of a graphical user interface on display 111.

Next, there may include a step 1202 where the processor 115 or other processor receives a selection of one of the selectable emotion icons 401. This may be based upon a user indication, for example, the user clicking on, tapping, or otherwise selecting one of the selectable emotion icons 401.

Subsequently, one or more of the selectable action icons are displayed on a graphical user interface of display 111 in a step 1203. In this instance, a first plurality of selectable action icons are shown on the graphical user interface, the first plurality of selectable action icons being chosen from a bank of a second plurality of selectable action icons, the first plurality of selectable action icons being determined based upon the received selection of the one of the plurality of selectable emotion icons. Further, the first plurality of selectable action icons is smaller in number than the second plurality of selectable action icons in the bank.

Figure 13:
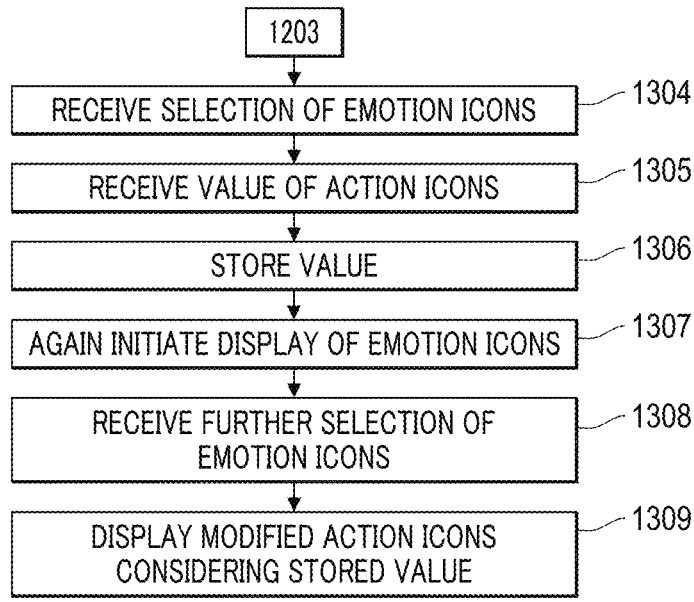
FIG. 13 is a flowchart of an example of an assessment and further actions performed by a processor subsequent to the method of FIG. 12 according to some embodiments.

As shown in FIG. 13, after performing steps 1201-1203, the method may include a step 1304 of receiving a selection of one or more of the selectable action icons. The selection may be received by the processor 115, or by a processor within the server 140. In step 1305, a value of the selectable action icon may be received. This may be an assessment as to whether or not the action indicated by the selectable action icon was considered to be helpful or otherwise acquire a positive association, based upon a user input of the same. The value may be stored either locally in the local memory 121, or in another memory such as server memory 145 or the memory of the administrator device 150.

At some later period, there includes a step of again 1306 initiating display of the emotion icons. This, for example, is an initiation of the processes shown in FIGS. 2-7 a subsequent time after the processes had been performed previously. In this case, there includes a step 1307 of receiving a further selection of the emotion icon. Then, in a step 1308, display of a modified (third plurality) of selectable action icons 601, 602, taking into consideration the value and/or other data, occurs.

Figure 14:
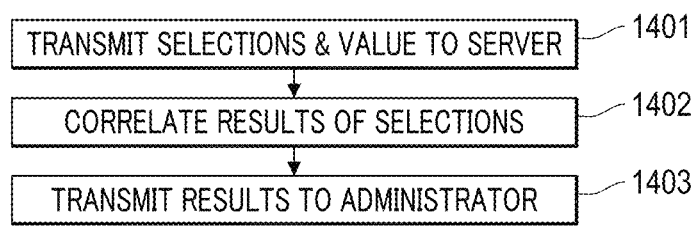
FIG. 14 is a flowchart of an example of providing information to an organization according to some embodiments.

Referring to FIG. 14, a step 1401 of transmitting one or more of the selected emotion icon, selected action icon, and the value (e.g., helpfulness determination) to the server 140 occurs. Thus, the server 140 can store the data remote from the user device 110, which can allow for a more standardized storage of data given that multiple user devices 110 are likely being used. Further, the server 140 will perform a step 1402 of calculating the results, which may take the form of the assessment and ranking changes described above, correlating all the results of the selections from the user, or may additionally or alternatively be adding all data from multiple user devices 110 together. In a step 1403, the data will be transmitted to the administrator to be received by the data reception module 163, so that the administrator can see and review the data. Prior to the results being transmitted, there may include an authentication process as described previously, confirming that an administrator viewing the administrator device is authorized to view the data.

While FIGS. 2-14 disclose details relating to a particular implementation whereby a user will select an emotion icon relating to an emotion, and the system will display an action icon accordingly, the instant application is not so limited. In some embodiments, instead of a user selecting a particular emotion, the system can determine a possible emotion of the user by receiving some input of an indicator not directly from a user's screen. For example, the system may utilize, for example sensors on a smart device or other device within a proximity of a user, so as to acquire data relating to the user. The indicator may be data about, for example, a user's heart rate or other indicators, which can be used to automatically suggest a potential emotion (e.g., stressed, angry or the like) without requiring an direct input from the user, though the system may also, after acquiring such information, optionally request confirmation of the user as to whether that emotion or other psychological or physiological characteristic is actually being felt. Such data can then be used by the system to provide an output to recommend an action (e.g., from a bank of potential recommended actions similar to the embodiments described with respect to FIGS. 2-14) based upon the algorithms discussed with respect to the embodiment of FIGS. 2-14. Such data can further be used for all implementations as described with respect to the embodiments of FIGS. 2-14, where instead of a chosen emotion icon is used, the data is used to carry out the described processes.

Further in some implementations, the system will obtain physiological data from the user without determining an emotion therefrom, and can recommend an action based upon the physiological data. As described above, the physiological data may be anything that indicates or represents some characteristic of the human body, such as blood pressure, heart rate, oxygen levels, blood sugar levels, insulin levels, breathing levels and/or other breathing characteristics, sleep data, and so on. The system may then, using the algorithms described with respect to the embodiments of FIGS. 2-14, provide a recommended action or actions accordingly.

Further and more generally, the system may utilize psychological data and/or indicators (including but not limited to data or indicators relating to emotions), physiological data and/or indicators, or both psychological data and/or indicators and physiological data and/or indicators, and using such data and/or indicators, make the appropriate assessments and provide the recommended action or actions accordingly.

Still further, while FIGS. 2-14 describe implementations where a user may input particular data to the system, which will then be utilize to provide recommendations of an action, the systems of the instant application are not so limited. In some embodiments, the system may learn that a certain user benefits from a particular action based upon its learning of psychological and/or physiological data from the past and/or other learning performed by the machine over a period of time, and can provide an automated, time-sensitive and proactive recommendation based upon the learned data. As an example, the system may ascertain, based upon previously received (via past input or otherwise learned) physiological data that the user benefits from stretching within 15 minutes after a blood pressure reaches a certain level. Thus, when the system determines that the blood pressure has reached that predetermined level, for example by using a blood pressure sensor, the system may proactively provide the action to stretch within 15 minutes based upon receiving the information. This may allow for a proactive, automatic (automated) wellness action, even without direct input from a user. This may also be beneficial insofar as it can allow for time-sensitive actions to be taken to improve wellness.

Additional advantages of the system and methods describe herein include allowing a user a motivation to perform wellness practices, and further ensuring that the actions that the user takes are not only optimized taking into consideration emotions that are felt and/or other determined psychological or physiological characteristics, but also empirical and past historical data regarding the user's, and perhaps other people's previous interactions with such an action. The real-time provision of different selectable icons from among a memory bank allow for a graphical user interface that includes optimal options for a user to be presented in a clear, color-coded and easy-to-understand way. The data compilation and calculation ensures that the user's own feelings and/or input relating to the action taken can be assessed and used in future rankings for the action, so that a subsequent graphical user interface can include optimized options for the user.

Further, the data is not only able to be shown in a compiled form to the user, but also to an organization, or a subgroup within an organization, to which the user has an association with. And, as described above, the data may be aggregated and assessed in a manner where additional recommendations may be provided. This may allow the organization to determine on its own, or receive from the systems of the instant embodiments, best practices taking into consideration what emotions or other physiological or psychological responses are being felt over a period of time, what actions have been taken, and which actions have the most positive response to the user base.

As will be appreciated by one skilled in the art, aspects of the present disclosure may be embodied as a system, method or computer program product. Accordingly, aspects of the present disclosure may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present disclosure may take the form of a computer program product embodied in one or more computer readable medium(s) having computer readable program code embodied thereon.

Any combination of one or more computer readable medium(s) may be utilized. The computer readable medium may be a computer readable signal medium or a non-transitory computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the non-transitory computer readable storage medium would include the following: a portable computer diskette, a hard disk, a random access memory (RAM), a read-only memory (ROM), an erasable programmable read-only memory (EPROM or Flash memory), a portable compact disc read-only memory (CD-ROM), an optical storage device, a magnetic storage device, or any suitable combination of the foregoing. In the context of this document, a non-transitory computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a non-transitory computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing. Computer program code for carrying out operations for aspects of the present disclosure may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present disclosure are described above with reference to flowchart illustrations and block diagrams of methods, apparatuses (systems) and computer program products according to embodiments of the disclosure. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

The flowcharts and block diagrams in the Figures illustrate the architecture, functionality, and operation of possible implementations of systems, methods and computer program products according to various embodiments of the present disclosure. In this regard, each block in the flowchart or block diagrams may represent a module, segment, or portion of code, which comprises one or more executable instructions for implementing the specified logical function (s). It should also be noted that, in some alternative implementations, the functions noted in the block may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems which perform the specified functions or acts, or combinations of special purpose hardware and computer instructions.

The following claims are in no way intended to limit the scope of embodiments to the specific embodiments described herein.

What is claimed is:

1. A system for instituting wellness practices, comprising:
at least one processor; and
at least one memory;
wherein the at least one processor is programmed to:
initiate display of a plurality of selectable wellness states on a graphical user interface, the plurality of selectable wellness states being provided by the processor based upon stored information;
receive a user selection of one of the plurality of selectable wellness states as a first selection input;
initiate display, on the graphical user interface, of a first output including a plurality of selectable action icons, each selectable action icon corresponding to a different action of a plurality of actions performable by the user, the plurality of selectable action icons being a subset chosen from a bank of potential selectable action icons stored in the at least one memory and being chosen taking into consideration the first selection input;
in response to the first output, receive a user selection of one of the plurality of selectable action icons, as a second selection input, the one of the selectable action icons identifying an action, of the plurality of actions, selected by the user to perform;
after receiving the user selection of the one of the plurality of selectable action icons, receive an assessment including a value input, from the user, of a value of the action selected by the user to perform;
request authentication from an administrative user, the administrative user having a higher authority level than the user;
authenticate an entry for the administrative user to access an application having an administrative graphical user interface that includes information regarding which wellness states users are experiencing, which ones of the users are experiencing ones of the wellness states, and which of the plurality of actions have been considered to be helpful by the ones of the users;
after authentication, display, via the application, the administrative graphical user interface including the information; and
after authentication, display, via the application, the administrative graphical user interface including a number of times certain actions of the plurality of actions were performed by the user, the user including a plurality of users.

2. The system according to claim 1, wherein the value input is received after a predetermined period of time from a time of the receiving of the selection of the one of the first plurality of selectable action icons and is stored in the memory.

3. The system according to claim 2, wherein the at least one processor is further programmed to initiate display, on the graphical user interface, of a second output including a new plurality of selectable action icons subsequent to the storing of the value input and in response to a further selection of the one of the plurality of selectable wellness states, the new plurality of selectable action icons being determined at least partially using learning based upon the received selection of the one of the plurality of selectable wellness states and the received value input.

4. The system according to claim 3, wherein the new plurality of selectable action icons is determined at least partially based upon previous history relating to the selectable action icons stored in the memory.

5. The system according to claim 1, wherein the selectable wellness states represents at least one of pulse, blood oxygen level, blood pressure, glucose level, heart rate or time since eating.

6. The system according to claim 1, wherein the at least one processor is further programmed to initiate display, on the graphical user interface, of a prompt regarding audio and/or visual perception prior to initiating the display of the first output.

7. The system according to claim 1, wherein the at least one processor is further configured to determine an amount of times each of the plurality of selectable wellness states have been selected within a predetermined period of time.

8. The system according to claim 1, wherein the processor is further configured to initiate display of at least some of the plurality of selectable wellness states in a first color, and at least some others of the plurality of selectable wellness states in a second color different from the first color.

9. The system according to claim 1, wherein the displayed certain actions are provided in rank order, ranked by a number of users performing the action in a predetermined time period.

10. The method according to claim 1, wherein the displayed certain actions are provided in rank order, ranked by a number of users performing the action in a predetermined time period.

11. The system according to claim 1, where the administrative graphical user interface includes a sort function to sort between specific practice participants and includes an option to view all schools, and includes a class function to sort between different classes within a school.

12. The system according to claim 1, wherein each of the plurality of selectable wellness states include a selectable emotion icon.

13. The system according to claim 1, wherein the at least one processor is further programed to provide an automated, time-sensitive action recommendation based upon past learning of psychological and/or physiological data.

14. A computer-implemented method for aiding in wellness, comprising:
initiating display of a plurality of selectable wellness states on a graphical user interface, the plurality of selectable wellness states being provided by the processor based upon stored information;
receiving a first selection input of a user selection of one of the plurality of selectable wellness states;
initiating display, on the graphical user interface, of a first output including a plurality of selectable action icons, each selectable action icon corresponding to a different action of a plurality of actions performable by the user, the plurality of selectable action icons being a subset chosen from a bank of potential selectable action icons stored in the at least one memory and being chosen taking into consideration the first selection input;

in response to the first output, receiving a second selection input of a user selection of one of the plurality of selectable action icons, the one of the selectable action icons identifying an action, of the plurality of actions, selected by the user to perform;

after receiving the user selection of the one of the plurality of selectable action icons, receiving an assessment including a value input, from the user, of a value of the action selected by the user to perform;

requesting authentication from an administrative user, the administrative user having a higher authority level than the user;

authenticating an entry for the administrative user to access an application having an administrative graphical user interface that includes information regarding which wellness states users are experiencing, which ones of the users are experiencing ones of the wellness states, and which of the plurality of actions have been considered to be helpful by the ones of the users;

after authentication, displaying, via the application, the administrative graphical user interface including the information; and after authentication, displaying, via the application, the administrative graphical user interface including a number of times certain actions of the plurality of actions were performed by the user, the user including a plurality of users.

15. The method according to claim 14, further comprising:

storing the received selection of the one of the plurality of selectable wellness states;

storing the value input;

modifying a relationship between the one of the plurality of selectable wellness states and the displayed output of the plurality of selectable action icons, the modifying being manifested by initiating display, on the graphical user interface, of a second output including a new plurality of selectable action icons subsequent to storing of the value input and in response to a further selection of the one of the plurality of selectable wellness states, the new plurality of selectable action icons being determined at least partially based upon the received selection of the one of the plurality of selectable wellness states and the received value input.

16. A system for instituting wellness practices, comprising: at least one processor; and at least one memory;

wherein the at least one processor is programmed to:

initiate display of a plurality of selectable wellness states on a graphical user interface, the plurality of selectable wellness states being provided by the processor based upon stored information;

receive a user selection of one of the plurality of selectable wellness states as a first selection input;

initiate display, on the graphical user interface, of a first output including a plurality of selectable action icons, each selectable action icon corresponding to a different action of a plurality of actions performable by the user, the plurality of selectable action icons being a subset chosen from a bank of potential selectable action icons stored in the at least one memory and being chosen taking into consideration the first selection input;

in response to the first output, receive a user selection of one of the plurality of selectable action icons, as a second selection input, the one of the selectable action icons identifying an action, of the plurality of actions, selected by the user to perform;

after receiving the user selection of the one of the plurality of selectable action icons, receive an assessment including a value input, from the user, of a value of the action selected by the user to perform; and immediately before the initiating display of the plurality of selectable wellness states on the graphical user interface, initiating display instructing a user to take a deep breath, and waiting a predetermined period of time before initiating the initiating the display of the plurality of selectable wellness states.

17. The system according to claim 16, wherein the processor is further configured to:

immediately after receiving the user selection of the one of the plurality of selectable wellness states as the first selection input and before the initiating display, on the graphical user interface, of the first output including a plurality of selectable action icons, initiating display instructing a user to identify what is seen and heard and to focus away from the display, and waiting a predetermined period of time before initiating the initiating display of the first output including the plurality of selectable action icons.

18. The system according to claim 16, wherein the at least one processor is further configured to:

request authentication from an administrative user, the administrative user having a higher authority level than the user;

authenticate an entry for the administrative user to access an application having an administrative graphical user interface that includes information regarding which wellness states users are experiencing, which ones of the users are experiencing ones of the wellness states, and which of the plurality of actions have been considered to be helpful by the ones of the users; and after authentication, display, via the application, the administrative graphical user interface including the information.

19. A system for instituting wellness practices, comprising: at least one processor; and at least one memory;

wherein the at least one processor is programmed to:

initiate display of a plurality of selectable wellness states on a graphical user interface, the plurality of selectable wellness states being provided by the processor based upon received information relating to at least one of a psychological or physiological indicator;

receive a user selection of one of the plurality of selectable wellness states as a first selection input;

initiate display, on the graphical user interface, of a first output including a plurality of selectable action icons, each selectable action icon corresponding to a different action of a plurality of actions performable by the user, the plurality of selectable action icons being a subset chosen from a bank of potential selectable action icons stored in the at least one memory and being chosen taking into consideration the first selection input;

in response to the first output, receive a user selection of one of the plurality of selectable action icons, as a second selection input, the one of the selectable action icons identifying an action, of the plurality of actions, selected by the user to perform;

request authentication from an administrative user, the administrative user having a higher authority level than the user;

authenticate an entry for the administrative user to access an application having an administrative graphical user interface that includes specific information; and after authentication, display, via the application, the administrative graphical user interface including the specific information, wherein the specific information includes an amount of times each of the plurality of selectable wellness states have been selected by a plurality of users within a predetermined period of time and a number of times certain actions of the plurality of actions were performed by the plurality of users within the predetermined period of time, the certain actions being displayed in rank order, ranked order, ranked by a number of users of the plurality of users performing the action in the predetermined time.

* * * * *